US011492753B2

(12) United States Patent
Smit et al.

(10) Patent No.: US 11,492,753 B2
(45) Date of Patent: *Nov. 8, 2022

(54) PROCESS FOR THE TREATMENT OF LIGNOCELLULOSIC BIOMASS (71) Applicant: Stichting Energieonderzoek Centrum Nederland, Petten (NL)

(72) Inventors: Adrianus Theodorus Smit, Petten (NL); Wouter Johannes Joseph Huijgen, Petten (NL); Rudie Johan Hendrik Grisel, Petten (NL)

(73) Assignee: NEDERLANDSE ORGANISATIE VOOR TOEGEPAST-NATUURWETENSCHAPPELIJK ONDERZOEK TNO, 'S-Gravenhage (NL)

( * ) Notice: Subject to any disclaimer, the term of this patent is extended or adjusted under 35 U.S.C. 154(b) by 137 days.

This patent is subject to a terminal disclaimer.

(21) Appl. No.: 14/768,073

(22) PCT Filed: Feb. 17, 2014

(86) PCT No.: PCT/NL2014/050095
§ 371 (c)(1),
(2) Date: Aug. 14, 2015

(87) PCT Pub. No.: WO2014/126471
PCT Pub. Date: Aug. 21, 2014

(65) Prior Publication Data
US 2016/0024712 A1  Jan. 28, 2016

(30) Foreign Application Priority Data

Feb. 15, 2013 (NL) ........................ 2010305
Jul. 15, 2013 (NL) ........................ 2011164

(51) Int. Cl.
*D21C 3/20* (2006.01)
*C12P 19/02* (2006.01)
*C13K 1/02* (2006.01)
*C07G 1/00* (2011.01)
*C13K 13/00* (2006.01)
*D21C 3/00* (2006.01)
*C08H 8/00* (2010.01)
*C08B 37/00* (2006.01)
*C08H 7/00* (2011.01)

(52) U.S. Cl.
CPC .............. *D21C 3/20* (2013.01); *C07G 1/00* (2013.01); *C08B 37/0057* (2013.01); *C08H 6/00* (2013.01); *C08H 8/00* (2013.01); *C12P 19/02* (2013.01); *C13K 1/02* (2013.01); *C13K 13/002* (2013.01); *D21C 3/00* (2013.01); *C12P 2201/00* (2013.01)

(58) Field of Classification Search
None
See application file for complete search history.

(56) References Cited

U.S. PATENT DOCUMENTS

| 2,022,654 A | 12/1935 | Dreyfus | |
| 4,470,851 A * | 9/1984 | Paszner | D21C 3/20 127/37 |
| 4,746,401 A * | 5/1988 | Roberts | D21C 3/222 162/72 |
| 5,730,837 A * | 3/1998 | Black | D21C 3/20 127/37 |
| 2009/0061495 A1 | 3/2009 | Beatty | |
| 2009/0176286 A1* | 7/2009 | O'Connor | C08B 37/0003 435/139 |
| 2009/0229599 A1* | 9/2009 | Zhang | D21C 3/22 127/1 |
| 2010/0163019 A1* | 7/2010 | Chornet | C13K 1/02 127/37 |
| 2010/0170504 A1* | 7/2010 | Zhang | D21C 5/00 127/37 |

(Continued)

FOREIGN PATENT DOCUMENTS

EP   2 336 193 A1   6/2011
WO   WO-03/062430 A1   7/2003
WO   WO-2007/120210 A2   10/2007

(Continued)

OTHER PUBLICATIONS

Corn Stover, Corn Stover by Vikram Koundinya, AgMRC, Webpage, 2019.*

(Continued)

*Primary Examiner* — Louise W Humphrey
*Assistant Examiner* — Srikanth Patury
(74) *Attorney, Agent, or Firm* — Foley & Lardner LLP (57) ABSTRACT Lignocellulosic biomass can be fractionated for the purpose of increasing cellulose purity in the pulp, increasing native lignin content of the isolated lignin, and improving cellulose hydrolysis, by performing the steps of: (a) extracting the biomass with an extracting liquid comprising at least 20 wt % of a first organic solvent at a temperature below 100° C.; (b) treating the extracted biomass with a treatment liquid comprising a second organic solvent selected from lower alcohols, ethers and ketones, optionally water and optionally an acid, at a temperature between 120° C. and 280° C., and, optionally: (c) subjecting a cellulose-enriched product stream resulting from step (b) to enzymatic hydrolysis. The first and second organic solvent may be different or the same; in particular they comprise ethanol or acetone.

23 Claims, 2 Drawing Sheets

(56) References Cited

U.S. PATENT DOCUMENTS

2015/0354018 A1    12/2015    Nishino et al.

FOREIGN PATENT DOCUMENTS

| WO | WO-2008/041840 A1 | 4/2008 |
| WO | WO-2010/074577 A1 | 7/2010 |
| WO | WO-2011/097720 A1 | 8/2011 |
| WO | WO-2012/000093 A1 | 1/2012 |
| WO | WO-2015/009145 A1 | 1/2015 |
| WO | PCT/EP2016/053271 | 2/2016 |

OTHER PUBLICATIONS

Zhao et al., Organosolv pretreatment of lignocellulosic biomass for enzymatic hydrolysis, Appl Microbiol Biotechnol,82:815-827, 2009 (Year: 2009).*

Zhang et al., Fractionating Recalcitrant Lignocellulose at Modest Reaction Conditions, Biotechnol. Bioeng. 2007;97: 214-223 (Year: 2007).*

Kumar et al., Methods for Pretreatment of Lignocellulosic Biomass for Efficient Hydrolysis and Biofuel Production, Ind. Eng. Chem. Res, Publication Date (Web): Mar. 20, 2009, 48(8):3713-3729, (Year: 2009).*

Abdul Khalil, H.P.S. et al., "Peer-reviewed article chemical composition, anatomy, lignin distribution, and cell wall structure of Malaysian plant waste fibers introduction", Bioresources 1(2), Nov. 4, 2006, pp. 220-232.

Bioresources.com et al., "peer-reviewed article optimization of lignin peroxidate, manganese peroxidase, and lac production from ganoderma lucidum under solid state fermentation of pineapple leaf introduction", BioResources, Nov. 26, 2012, pp. 250-271.

Cybulska, I. et al., "Catalyzed modified clean fractionation of prairie cordgrass integrated with hydrothermal post-treatment", Biomass and Bioenergy, vol. 46, Nov. 1, 2012, pp. 389-401.

Dachun, G. et al., "Development of an integrated pretreatment fractionation process for fermentable sugars and lignin: Application to almond () shell*", Biomass and Bioenergy, Pergamon, Amsterdam, NL, vol. 35, No. 10, Aug. 24, 2011, pp. 4435-4441.

Huijgen et al., "Fractionation of what straw by prehydrolysis, organosolv delignification and enzymatic hydrolysis for production of sugars and lignin", Bioresource Technology, vol. 114, Mar. 7, 2012, pp. 389-398.

International Search Report of PCT/NL2014/050095 dated Apr. 16, 2014.

Ming-Fei, L. et al., "Formic acid based organosolv pulping of bamboo (): Comparative characterization of the dissolved lignins with milled wood lignin", Chemical Engineering Journal, Elsevier Sequoia, Lausanne, CH, vol. 179, Oct. 20, 2011, pp. 80-89.

Nordin et al., "Chemical elemental characteristics of biomass fuels", Biomass and Bioenergy, Pergamon, Amsterdam, NL, vol. 6, No. 5, Jan. 1, 1994, pp. 339-347.

Omojasola, P.F. et al., "Cellulase production by some fungi cultured on pineapple waste", Nature and Science, 6(2), Jan. 1, 2008, pp. 64-79.

Papatheofanous, M.G. et al., "Two-stage acid-catalyzed fractionation of lignocellulosic biomass in aqueous ethanol systems at low temperatures", Bioresource Technology 54, Issue 3, Jan. 1, 1995, pp. 305-310.

Phillips, M. et al., "The chemistry of lignin. IX. Lignin from Barley Straw", Journal of the American Chemical Society, vol. 56, Dec. 1, 1934, pp. 2707-2710.

Sun, F. et al., "Enhanced enzymatic hydrolysis of wheat straw by aqueous glycerol pretreatment", Bioresource Technology, Elsevier BV, GB, vol. 99, No. 14, Sep. 1, 2008, pp. 6156-6161.

Abels et al., "Membrane processes in biorefinery applications", Journal of Membrane Science, 2013, vol. 444, pp. 285-317.

Garcia et al., "Energy and economic assessment of soda and organosolv biorefinery processes", Biomass and Bioenergy, 2010, pp. 1-10.

Ghose, "Measurement of cellulose activities", Pure & Applied Chemistry, vol. 59, 1987, No. 2, pp. 257-268.

Gonzalez Alriols et al., "Combined organosolv and ultrafiltration lignocellulosic biorefinery process", Chemical Engineering Journal, 2009, pp. 1-8.

Huijgen et al., "Pretreatment and fractionation of wheat straw by an acetone-based organosolv process", Industrial & Engineering Chemistry Research, 2010, vol. 49, No. 20, pp. 10132-10140.

International Search Report issued in International Patent Application No. PCT/EP2016/053271, dated May 18, 2016.

International Search Report issued in International Patent Application No. PCT/NL2014/050481 dated Sep. 17, 2014.

Perez et al., "Selective acetone-water delignification of Eucalyptus urograndis: An alternative towards the biorefinery approach", The Open Agriculture Journal, 2010, vol. 4, pp. 145-152.

Wildschut et al., "Ethanol-based organosolv fractionation of wheat straw for the production of lignin and enzymatically digestible cellulose", Bioresource Technology, 2013, vol. 135, pp. 58-66.

Zhang et al., "Organosolv pretreatment of plant biomass for enhanced enzymatic saccharification", Green Chemistry, Jan. 2016, pp. 1-23.

Zhao et al., "Organosolv pretreatment of lignocellulosic biomass for enzymatic hydrolysis", Appl. Microbiol Biotechnol, 2009, vol. 82, pp. 815-827.

U.S. Appl. No. 14/905,258, US 2016-0152736 A1.

* cited by examiner

PROCESS FOR THE TREATMENT OF LIGNOCELLULOSIC BIOMASS

CROSS-REFERENCE TO RELATED APPLICATIONS

This application is the National Phase of International Patent Application No. PCT/NL2014/050095, filed Feb. 17, 2014, published on Aug. 21, 2014 as WO 2014/126471 A1, which claims priority to Netherlands Application No. 2010305, filed Feb. 15, 2013, and Netherlands Application No. 2011164, filed Jul. 15, 2013. The contents of which are herein incorporated by reference in its entirety.

The present invention relates to an advanced process for the fractionation of lignocellulosic biomass using organosolv.

BACKGROUND

Biomass, especially lignocellulosic biomass, is a valuable resource for the production of (bio)fuels, chemicals, performance products and energy. Lignocellulose is the most abundant renewable biomass available on land, and therefore relatively cheap. It comprises mainly cellulose, hemicellulose and lignin. Many research efforts have been devoted to the development of processes for the cost-effective conversion of biomass, especially lignocellulosic biomass, to valuable compounds. An example thereof is the conversion of cellulose to glucose, which in turn may serve e.g. as a precursor for 'second-generation' bioethanol (by fermentation of glucose), and is thus suitable for the preparation of biofuels.

The main structural components of biomass are cellulose, hemicelluloses and lignin. The two main types of hemicelluloses are xylans (xylose ($C_5$) backbones, sometimes substituted with arabinose or glucuronic acid side groups), which are predominant in hardwood and grasses, and (gluco)mannans (glucose-mannose ($C_6$), ratio about 1:3, backbones sometimes substituted with galactose side groups), which are predominant in softwood. Minor hemicellulose types include xyloglucans, arabino-galactans, and mixed β-1,3-glucans. Hemicelluloses may be chemically linked to lignin. Table 1 below gives approximate compositions of the structural components of some biomass types.

TABLE 1

Compositions of the structural components of some biomass types (in wt % based on dry weight)

|  | cellulose | mannans | xylans | other polysaccharides | lignin |
| --- | --- | --- | --- | --- | --- |
| softwood | 35-40 | 15-20 | 5-10 | 3-10 | 25-32 |
| hardwood | 40-50 | 1-4 | 15-30 | 2-5 | 22-30 |
| grasses, straws | 33-40 | 0-2 | 20-27 | 3-8 | 20-32 |

The so-called organosolv process, referred to herein as step (b) of the process of the invention, can be used to treat biomass (pretreatment), in order to make cellulose polymers better accessible for hydrolytic enzymes converting cellulose to glucose, or for pulping or fractionating of the biomass. Without pre-treatment, the cellulose within lignocellulose biomass is poorly accessible for the hydrolytic enzymes, as it is shielded by other biomass components such as lignin and hemicelluloses. Organosolv involves high-temperature treatment of the biomass with a (water-miscible) organic solvent and optionally an (acidic) catalyst. During organosolv, the lignocellulose biomass is fractionated into a cellulose-enriched solid product stream (pulp) and a liquid product stream (liquor) comprising lignin and hemicellulose derivatives.

The hemicelluloses present in the lignocellulosic biomass are relatively unstable and break down during organosolv, especially as a result of the elevated temperatures employed. Hemicellulose is first hydrolysed into sugar monomers ($C_5$ and/or $C_6$ sugars), which may subsequently dehydrate to furans such as furfural, and react further to other compounds (including condensation products with lignin ("pseudo-lignin")). Most of these latter compounds are less valuable than hemicellulose itself or the products directly obtained from it such as monomeric sugars and furfural. Potentially valuable compounds that can be derived from the hemicellulose (e.g. monomeric sugars and furfural) are thus lost, thus reducing the effectiveness of the conversion of biomass into valuable components. In addition, these degradation products may pollute the cellulose stream and/or the lignin stream, which are produced by the organosolv process, thereby reducing the efficiency of further treatment of these streams to produce valuable end-products, such as ethanol.

Especially the cellulose-enriched product stream obtained from the organosolv process comprises many impurities. Although organosolv treatment separates large parts of lignin and hemicellulose from the cellulose pulp, the cellulosic pulp typically still comprises significant amounts of lignin, as well as pseudo-lignins which may have been formed during pretreatment by reaction of lignin with e.g. proteins, other extractives and/or furfural. These impurities significantly hamper the enzymatic hydrolysis of cellulose to glucose, which is to date only scarcely applied on a commercial scale (the first plant ever opened in October 2013 in Crescentino, Italy), since it cannot compete yet with glucose produced from first generation biomass sources (starch, sucrose etc.), in view of the high costs of the pretreatment step and required amounts of enzyme.

Alternatives to enzymatic hydrolysis of cellulose, e.g. concentrated acid treatment, are undesirable for environmental reasons, corrosion of equipment and associated costs, and because they yield more by-products by sugar degradation reactions. Hence, one of the challenges of current research is to find means to enhance the efficiency of enzymatic hydrolysis of cellulose, in order to allow application on an industrial scale.

SUMMARY OF THE INVENTION

The invention relates to an advanced organosolv process of lignocellulosic biomass, resulting in a cellulose-enriched product (pulp) containing less impurities and a lignin-enriched product containing a higher content of native lignin. Surprisingly, the inventors have found that performing an extraction with an organic solvent prior to organosolv fractionation results in a better performance of the organosolv step itself. Moreover, using pre-extracted biomass according to the invention allows a more efficient enzymatic hydrolysis of cellulose and thus a reduction of the required enzyme load and associated costs. Furthermore, the composition of the products obtained from the organosolv process according to the invention is less influenced by the compositional differences of various types of biomass or various batches of the same type of biomass. These variations are suppressed by removal of (large parts of) the extractives by organic solvent (and optionally aqueous) extraction.

DETAILED DESCRIPTION

The invention relates to a process for fractionating lignocellulosic biomass into a cellulose-enriched product stream (pulp) and a lignin-enriched product stream (liquor), comprising extracting the biomass and subsequently subjecting the extracted biomass to an organosolv step. Without being bound by a theory, it is believed that pre-extraction of the biomass using an organic solvent removes biomass components (extractives) which hamper the organosolv process and/or the subsequent enzymatic cellulose hydrolysis, but leaves the valuable structural components (cellulose, hemicellulose and lignin) intact.

Thus, the invention relates to a biomass fractionation process, comprising:
(a) extracting the biomass with an extracting liquid comprising at least 20 wt % of a first organic solvent at a temperature below 100° C.;
(b) treating the extracted biomass with a treatment liquid comprising a second organic solvent selected from lower alcohols, ethers and ketones, optionally water and optionally an acid, at a temperature between 120° C. and 280° C.

Biomass suitable for the process according to the invention includes lignocellulosic biomass, such as softwood, hardwood, and herbaceous biomass, including grasses and straws, and can be supplied in the form of forestry residues and products (e.g. trees), crops (e.g. energy crops such as grasses and short rotation coppice wood), agricultural residues, yard waste, animal and human waste (e.g. biodegradable municipal waste), advantageously in the form of forestry residues, agricultural residues, yard waste, animal and human waste. Such biomass comprises in general 20 to 80 wt. % carbohydrates (based on dry matter), which are valuable starting materials for production of fuels and chemicals in a biorefinery.

Lignocellulosic biomass (so-called second generation biomass) is cheaper than starch-containing biomass (first generation biomass) and does not compete with (human) dietary needs. Preferably, herbaceous biomass in the form of agricultural residues and/or biodegradable municipal waste is used in the process according to the invention, more preferably, the herbaceous biomass is selected from straw, leaves, (fresh or dried) grasses and combinations thereof, most preferably straw (e.g. rice straw, barley straw, wheat straw).

Extraction and Pre-Extraction

Extraction comprises at least one extraction step wherein the biomass is extracted with an extraction liquid comprising a first organic solvent (referred to as organic extraction). In one embodiment, extraction contains only one extraction step, wherein the biomass is extracted with an extraction liquid comprising a first organic solvent, optionally as a mixture with water. Extraction may also involve multiple extraction steps, wherein the extraction liquid in each individual extraction step comprises water or a first organic solvent or a mixture thereof. Thus, extraction may contain at least one, at least two, at least three, or at least four separate extraction steps. Preferably, extraction contains at least two extraction steps, more preferably it contains two extraction steps. It is preferred that each individual extraction step is performed using a different extraction liquid.

Conveniently, at least one extraction step is performed using water as an extraction liquid and one or more other extraction steps are performed using a first organic solvent and/or mixtures of water and a first organic solvent as extraction liquid. The extraction liquid of the organic extraction step(s) comprises a first organic solvent, preferably comprises at least 20 wt % of the first organic solvent (i.e. between 20 wt % and 100 wt %), more preferably at least 50 wt %, even more preferably at least 70 wt %, even more preferably at least 90 wt %, most preferably at least 95 wt %. The extraction liquid preferably comprises at most 50 wt % water (i.e. between 0 wt % and 50 wt %), more preferably at most 30 wt %, even more preferably at most 10 wt %, most preferably at most 5 wt %. Whenever it is mentioned that the extraction liquid is a certain solvent, it is meant that the extraction liquid comprises at least 90 wt % of that solvent, preferably at least 95 wt %.

In case the extraction comprises two or more extraction steps, it is preferred that one extraction step is performed using water as extraction liquid (i.e. containing less than 20% of organic solvent), and the other extraction step is an organic extraction step, wherein the extraction liquid comprises a first organic solvent, preferably ethanol, as extraction liquid. This organic extraction is advantageously performed using at least 20%, preferably at least 50%, more preferably at least 70% of the first organic solvent. In a most preferred embodiment, the extraction contains two extraction steps, a first extraction step, referred to below as pre-extraction, wherein the biomass is extracted with water as extraction liquid (i.e. an aqueous extraction step), and a second extraction step, wherein the water-extracted biomass is extracted with a first organic solvent as extraction liquid, wherein the first organic solvent is preferably a water-miscible organic solvent, more preferably ethanol (i.e. an organic extraction step).

Suitable first organic solvents to be used according to the invention include, but are not limited to, lower alcohols and diols, ethers, ketones, amides, lower alkanes, carboxylic acids and $CO_2$ (sc), preferably lower alcohols and diols, ethers and ketones. Herein, "lower" means containing 1-6 carbon atoms ($C_1$-$C_6$), especially $C_1$-$C_4$. The first organic solvent is preferably water-miscible or capable of dissolving at least 10 wt % of water, based on total weight of the first organic solvent including any amount of water.

Examples of suitable first organic solvents include methanol, ethanol, propanol, isopropanol, butanol and its isomers, ethylene glycol, propylene glycol, methoxyethanol, dimethoxyethane, diethylene glycol, dioxane, acetone, methyl ethyl ketone, tetrahydrofuran, dimethyl formamide, dimethyl acetamide, N-methylpyrrolidone, and mixtures thereof. Further polar (co)solvents can be used as well, although these are slightly less preferred, for example acetonitrile, formic acid, acetic acid, methyl acetate, ethyl acetate, non-apolar haloalkanes such as dichloromethane, and $CO_2$ (sc).

Apolar solvents, such as hydrocarbons, e.g. pentane, cyclopentane, hexane, toluene or mixtures thereof, such as petroleum ether, can be also used as (co)solvents, or as solvents in an optional post-extraction step. In the context of the present invention, mixtures of miscible organic solvents are also encompassed in the term "organic solvent". Preferably, the first organic solvent is selected from methanol, ethanol, propanol, butanol, acetone and mixtures thereof, more preferably the first organic solvent comprises at least ethanol, most preferably the first organic solvent is ethanol. Conveniently, at least one extraction step of the extraction is performed using an extraction liquid comprising a first organic solvent, which is the same organic solvent to be used during the subsequent organosolv step (referred to as the second organic solvent, see further below). Preferably, the extraction liquid comprises ethanol as first organic solvent, most preferably the extraction liquid is ethanol.

For the optional pre-extraction step and other optional aqueous extraction steps during the one or more individual extraction steps of step (a) of the process according to the invention, it was found that (non-demineralised) tap water or filtered, relatively clean water, can be conveniently used as extraction liquid, while demineralised water is also suitable, with or preferably without added organic solvents or other additives. Alternatively, the water may originate from a waste stream of the process according to the invention, in particular from the organosolv step. Conveniently, water is isolated from the liquor after lignin precipitation and separation of the hemicellulose derivatives, and may be used after optional further purification in an aqueous (pre-) extraction step.

Aqueous (pre-)extraction steps may be performed using an aqueous extracting liquid, in particular water. The aqueous liquid may contain agents assisting in the dissolution of extractives, such as acids, bases, salts and surfactants. The pH may be from slightly alkaline to acidic, e.g. between 2 and 10, preferably between 4 and 8. If desired, minor amounts of an organic solvent (e.g. as described above for the first organic solvent, alcohols, polyols, ethers and the like) may be added to the aqueous extracting liquid. However, the level of organic solvents is preferably kept low, e.g. below 20 wt %, more preferably below 10 wt %, most preferably below 2 wt %.

The biomass subjected to the extraction step (a) may be fresh or dried biomass, optionally after removal of large impurities such as stones and pieces of metal, and optionally chopped or milled to pieces for ease of handling (e.g. pieces of 0.01 to 50 cm, in particular 0.1 to 10 cm in length or diameter, depending on the type of biomass).

Each individual extraction step of the extraction may be performed using any extraction technique known in the art. Conveniently, extraction is performed by washing the biomass with the solvent, or by soaking the biomass in the solvent. In this embodiment, the biomass preferably soaks at least 1 minute in the solvent, more preferably between 5 minutes and 600 minutes, most preferably between 10 minutes and 120 minutes. The extraction may also be performed stage-wise, in a counter-current mode. In such a staged mode, relatively clean solvent is used for a second or later stage of the extraction and the extract of the second or later stage is used as an extracting liquid for the preceding (or first) stage. In this way the residual amount of extractives in the biomass is minimised while keeping the amount of extracting liquid relatively low. Counter-current extraction allows a reduction in the total amount of extraction solvent.

Each extraction step of the extraction can be performed with water and/or first organic solvent as extracting liquid, wherein the extracting liquid has a temperature between its melting temperature and its boiling temperature (or higher if pressurised), i.e. is in liquid form. Preferred extracting temperatures are from 10 to 100° C. For aqueous extraction steps, the extraction temperature is more preferably from 15 to 75° C., most preferably from 20 to 60° C., and for organic extraction steps more preferably from 15 to 80° C., even more preferably from 30 to 75° C., most preferably from 50 to 75° C. For extraction steps using a mixture of water and organic solvent, the skilled person will appreciate how to manipulate the temperatures for optimal results.

For extraction step (a), i.e. using a first organic solvent, the amount of extracting liquid is preferably between 0.5 and 20 L of liquid per kg of biomass. For single stage extraction, the preferred amount is between 1 and 12 L, most preferred between 1.5 and 6 L of solvent per kg of biomass. For the optional aqueous pre-extraction step, the amount of extracting liquid (water) is preferably between 1 and 20 L of liquid per kg of biomass. For single stage extraction, the preferred amount is between 2 and 12 L, most preferred between 3 and 10 L of solvent per kg of biomass. For counter-current extraction, the preferred amount of extraction solvent is between 1 and 6 L, especially between 1.5 and 4 L solvent per kg biomass. The biomass weight is understood herein as the dry weight, without adherent water.

As will be immediately appreciated by the skilled person, extraction implies separation of the extraction liquid from the extracted material. Thus, the extracted biomass is separated from the extraction liquid before the extracted biomass is fed to the next step in the process, e.g. a subsequent extraction step or an organosolv step (b) as described below. Such separation may conveniently be performed by filtering the mixture of extracted biomass and extraction liquid after each extraction step of the extraction, using a filter having small enough pores to retain the chopped and washed or soaked biomass, and large enough pores to allow the extract comprising extractives to pass. Typically, the pores of such a filter are between 10 λm and 10 mm in diameter, preferably between 100 μm and 1 mm. The retentate comprising biomass is used for further treatment by organosolv as described below.

During extraction, the total dry weight of the biomass may reduce, as water-soluble and/or organic solvent-soluble components will be washed away. These extractives may include salts, proteins, fatty acids, triglycerides, waxes, terpenes and resin acids. As the skilled person will appreciate, hydrophilic components (e.g. salts, water-soluble proteins) will predominantly be washed away during aqueous extraction, i.e. in the pre-extraction step, while lipophilic components (e.g. lipophilic proteins, fatty acids, triglycerides, waxes, terpenes and resin acids) are predominantly extracted during extraction with an organic solvent. The composition and concentration of washable components is highly dependent on the type of biomass. For example, annual fibres such as straw contain relatively large amounts of fatty acids and/or waxy materials, which may be extracted using organic solvent, and (soft)wood may contain significant amounts of lipophilic terpenes and resin acids.

Organosolv

The extracted biomass is subsequently fed to an organosolv process step, which separates the lignocellulose biomass into a cellulose-enriched product stream (also referred to as 'cellulose pulp' or just 'pulp') and a lignin-enriched product stream (liquor). During organosolv, the extracted biomass is treated with a treatment liquid, comprising a second organic solvent, water and optionally at most 5 wt % of an acid.

Any organosolv process step as known in the art may be employed in the process according to the invention. The organosolv step according to the invention typically involves heating the suspension of the extracted biomass and the treatment liquid to a temperature above 100° C., such as between 100° C. and 280° C., preferably between 120° C. and 280° C., more preferably between 125° C. and 280° C., more preferably between 125° C. and 250° C., even more preferably between 150° C. and 240° C., most preferably between 170° C. and 220° C., and/or at a pH below 6.0, preferably between 1.0 and 5.0, more preferably between 2.0 and 5.0.

Typically, organosolv is performed either autocatalytically or acid-catalysed. Autocatalytic organosolv is performed by exposing lignocellulose biomass, which is suspended in a (water-miscible) second organic solvent optionally combined with water, to elevated temperatures, typically above 180° C., preferably above 190° C. During acid-catalysed organosolv, the temperature may be somewhat lower, typically above 170° C., and some acid is added to the suspension of the biomass, the second (water-miscible) organic solvent and optionally water. In the context of the present invention, any organosolv step at a temperature above 170° C., either autocatalytic or acid-catalysed, is referred to as high temperature organosolv.

The process according to the invention is especially useful for low temperature organosolv processes, i.e. organosolv performed at a temperature below 170° C., such as between 100° C. and 170° C., preferably between 120° C. and 170° C., more preferably between 120° C. and 165° C., most preferably between 130° C. and 160° C. In specific embodiments the organosolv process is performed at temperature below 140° C., e.g. between 120 and 139° C., more preferably between 120° C. and 135° C. Low temperature organosolv is especially desirable for two reasons. First of all, it reduces the costs of the pretreatment step, and secondly it reduces degradation of the hemicellulose to undesired by-products (e.g. furfural and humins) and less formation of pseudo-lignins (e.g. by reaction of xylan and xylose degradation products with lignin). As discussed above, hemicellulose degradation during pretreatment significantly reduces the effectiveness of the conversion of biomass into valuable components. However, at those reduced temperatures, non-structural organic components present in biomass may negatively affect the organosolv process.

During high temperature organosolv (i.e. above 170° C.), the non-structural components of the biomass, when not extracted prior to organosolv, decompose or react with structural components. As these non-structural organic components or extractives are largely removed using the extraction step according to the invention, the organosolv process operates more smoothly, even at reduced temperatures. This is especially true for the low temperature organosolv process of annual fibres such as straw, which comprise significant amounts of apolar extractives such as fatty acids and waxy materials. At the temperatures employed during low temperature organosolv, these apolar extractives form aggregates during the organosolv process, thereby hindering the fractionation. It was observed that low temperature organosolv of wheat straw was less effective without prior extraction with an organic solvent.

Suitable second organic solvents for the organosolv step are known in the art and include lower alcohols, ketones and ethers, preferably lower alcohols, ketones and ethers, such as methanol, ethanol, (iso)propanol, butanol, ethylene glycol, methoxyethanol, dimethoxyethane, dioxane, acetone, methyl ethyl ketone. The second organic solvent may be a pure organic solvent, but may also be a mixture of organic solvents, preferably the second organic solvent is a pure organic solvent. A compound is considered to be a solvent in the context of the present invention, when it is liquid under the process conditions of the organosolv reaction, preferably when it is liquid under ambient conditions. Moreover, the solvent is preferably not an apolar solvent, and hence hydrocarbons and non-polar halogenated hydrocarbons are preferably not included in the second organic solvent.

In particular, the second organic solvent preferably contains at least an oxygen and/or nitrogen-containing moiety, preferably selected from alcohol, ether, ketone, ester, amine, amide, imide, cyanide and nitro functions. More preferably, the second organic solvent contains a moiety containing at least an oxygen atom, preferably selected from alcohol, ether, ketone and ester functions. It is especially preferred that the second organic solvent does not comprise a carboxylic acid containing solvent. The presence of large amounts of acid during organosolv is highly undesirable, first of all as this may cause heavy corrosion of the equipment and reactor, and secondly because unwanted solvent losses occur in view of side-reactions that occur between lignocellulose constituents and carboxylic acids. However, a catalytic amount of acid is optionally present in addition to the second organic solvent, as described below. Preferred second organic solvents include ethanol and acetone. In a preferred embodiment, the solvent used during the organosolv step is the same solvent as used as first organic solvent in the extraction step, as discussed above.

In case the process according to the invention employs low temperature organosolv, the second organic solvent preferably does not comprise a hydroxylic organic solvent, but at least one non-hydroxylic organic solvent. In case the second organic solvent is a mixture of two or more organic solvents, it is preferred that at least one organic solvent is a non-hydroxylic organic solvent, more preferably all organic solvents that make up the second organic solvent are non-hydroxylic solvents. Performing organosolv at low temperature with a non-hydroxylic solvent gives less unwanted side-reactions which would be accompanied by undesired solvent losses, such as alkoxylation of hemicellulose or xylose to by-products (e.g. xylosides) and "pseudo-lignin" formation (e.g. by alkoxylation or ethoxylation), compared to low temperature organosolv using an alcoholic organic solvent, in particular ethanol.

Suitable non-hydroxylic organic solvents include all organic solvents which are known in the art to be suitable for organosolv, as discussed above, except all hydroxylic solvents. Especially polar non-hydroxylic solvents are suitable. In the context of the present invention, "hydroxylic solvents" comprise at least one hydroxyl moiety (OH group), such as alcohols, such as methanol, ethanol, (iso)propanol, butanol, ethylene glycol, methoxyethanol, or organic solvents comprising a carboxylic acid moiety (COOH group), such as formic acid, acetic acid, peracetic acid and haloacetic acids. Non-hydroxylic solvents thus do not comprise a hydroxyl moiety.

Preferably, the non-hydroxylic solvent comprises an ether moiety and/or a carbonyl moiety, such as a ketone moiety, an ester moiety or an amide moiety, more preferably the non-hydroxylic solvent comprises at least a ketone moiety and optionally one or more selected from an ether moiety, an ester moiety and an amide moiety. Preferably, the non-hydroxylic organic solvent is selected from ethers and ketones, more preferably the non-hydroxylic organic solvent is a ketone. Ketones are especially preferred in view of the high solubility of lignin in ketone solvents. Preferred ethers include dimethoxy ethane, tetrahydrofuran (THF), 1,4-dioxane and 1,3-dioxolane. Preferred ketones include acetone, butanone (methyl ethyl ketone or MEK), methyl isobutyl ketone (MIBK), cyclohexanone, acetoacetic (3-oxo-butanoic) acid esters, and levulinic (4-oxopentanoic) esters, such as methyl levulinate and ethyl levulinate.

In an especially preferred embodiment, the non-hydroxylic organic solvent is selected from acetone and ethyl levulinate, most preferably the non-hydroxylic organic solvent is acetone. The treatment liquid preferably comprises at least 20 wt % of the second organic solvent, more preferably 20-95 wt %, even more preferably 25-80 wt %, even more preferably 40-70 wt %. most preferably 45-65 wt %, based on total weight of the treatment liquid.

The treatment liquid further preferably comprises water. The presence of water in the treatment liquid allows hydrolysis reactions to take place during organosolv, in order to break up the network of structural components. Preferably, the treatment liquid comprises at least 5 wt % water, more preferably between 20 wt % and 80 wt % water, even more preferably between 30 wt % and 60 wt % water, most preferably between 35 wt % and 65 wt % water, based on total weight of the treatment liquid. In the treatment liquid, the weight ratio of the organic solvent to water is preferably between 20/80 and 80/20, more preferably between 30/70 and 75/25, even more preferably between 40/60 and 70/30, most preferably between 40/60 and 65/35.

The treatment liquid may further comprise an acid, in particular when employing high temperature acid-catalysed organosolv at a temperature between 170° C. and 200° C., or low temperature organosolv at a temperature below 170° C. Generally, the desired amount of acid increases as the temperature at which the organosolv step is performed decreases. Typically, the pH of the suspension of treatment liquid and extracted biomass during organosolv is below 7.0, preferably below 6.0, more preferably between 0.5 and 5.5, even more preferably between 1.0 and 5.0, most preferably between 1.5 and 4.0, to enable optimum fractionation to cellulose pulp and lignin-containing liquor.

The amount of the acid can be defined in various ways. Firstly, the amount of acid may be defined as a concentration by weight, such as at most 5.0 wt % acid based on total weight of the treatment liquid, preferably between 0.01 wt % and 4.0 wt %, more preferably between 0.05 and 2.5 wt %, most preferably between 0.1 and 1.5 wt %, based on total weight of the treatment liquid, or the amount of acid may be defined as a molar concentration within the treatment liquid, such as at most 250 mM acid, preferably between 1 and 200 mM, more preferably between 10 and 150 mM.

Alternatively, the amount of acid can be defined as acid equivalents, such as at most 500 meq, preferably between 2 and 400 meq, more preferably between 10 and 250 meq of an acid having a pKa of 4.5 or lower, wherein a meq is defined as a mmol of hydrogen ions per L of treatment liquid. As a further alternative, the amount of acid can be defined in relation to the amount of biomass treated, such as at most 300 g acid, preferably 0.5-250 g acid, more preferably 5-200 g, most preferably 10-125 g per kg of dry weight of the biomass, or such as at most 5.0 mol, preferably 5 mmol-3.0 mol acid preferably 50 mmol-2.5 mol, more preferably 100 mmol-1.5 mol per kg of dry weight of the biomass, wherein 1 L of treatment liquid is used per 20-10000 g dry weight of biomass. Amounts of acid in the treatment liquid above the upper limits may result in more side-reactions, and thus the formation of more impurities, during organosolv. As the skilled person appreciates, the amount of acid which is used for optimum performance of the organosolv reaction may vary depending on the strength of the acid (pKa) and the acid neutralisation capacity of the biomass. Conveniently, the acid is comprised in the treatment liquid before this is added to the extracted biomass, but the acid may also be added separately to the suspension of biomass in the treatment liquid.

Suitable acids include organic acids and inorganic acids. Preferred acids have a pKa value of 4.5 or lower, preferably a pKa value of 3.0 or lower, most preferably a pKa value of 1.0 or lower. Acids with such low pKa values are preferred, as a lower amount is needed to enable efficient organosolv fractionation of the biomass, when compared to acids having a higher pKa value. Suitable acids include sulfuric acid, sulfurous acid, hydrochloric acid, phosphoric acid, perchloric acid, sulfonic acids such as methanesulfonic acid and para-toluenesulfonic acid, formic acid, oxalic acid, benzoic acid, lactic acid, malonic acid, maleic acid, dichloroacetic acid, trichloroacetic acid, trifluoroacetic acid, and combinations thereof.

As carboxylic acids are more prone to side-reactions than acids which do not comprise a carboxyl group, such as inorganic acids, the use of non-carboxylic acids or even inorganic acids is especially preferred. Thus, preferably the acid is selected from sulfuric acid, sulfurous acid, hydrochloric acid, phosphoric acid, para-toluenesulfonic acid, and combinations thereof. Most preferably, sulfuric acid is used. Herein, "the acid" may refer to a single compound, or to a mixture of different acids. Preferably, a single acid is used.

Typically, the suspension of biomass and treatment liquid is obtained by mixing at most 50 L and at least 0.1 L of treatment liquid per kg dry weight of the biomass, preferably between 1.0 L and 20 L, even more preferably between 3 L and 15 L, most preferably between 3 L and 8 L. Thus organosolv treatment of biomass uses 1 L of treatment liquid as defined below per 20 g to 10 kg of biomass, preferably per 50 to 1000 g, even more preferably per 67 to 333 g of biomass, most preferably per between 125 and 333 g of biomass (dry weight). The optimum ratio of treatment liquid to biomass will depend on the type of biomass.

A major advantage of the organosolv process according to the present invention is the formation of product streams with higher purity (fewer impurities), when compared to prior art organosolv processes, and a higher yield in monomeric, oligomeric and polymeric saccharides. This is especially true in case the organosolv process according to the invention is combined with hydrolysis of the cellulose pulp, which converts polymeric and oligomeric saccharides to monomeric saccharides, as such obtaining high yields of monomeric saccharides based on total carbohydrates present in biomass.

Organosolv yields a cellulose pulp and a separate lignin-containing liquor. The cellulose pulp obtained by the process according to the invention contains a higher content of cellulose (i.e. the cellulose pulp has a higher purity), compared to cellulose pulp obtained by prior art organosolv processes. For example, the lignin content of the cellulose pulp is reduced, when compared to prior art cellulose pulp. Hence, the invention also relates to the products obtainable by the process according to the invention.

Typically, the cellulose pulp according to the invention is a composition comprising, based on total dry weight:
(a) at least 65 wt % cellulose, preferably at least 70 wt % cellulose, more preferably at least 75 wt % cellulose;
(b) at most 12 wt % lignin, preferably at most 9 wt % lignin, more preferably at most 8 wt % lignin, most preferably at most 6 wt % lignin;
(c) preferably at most 6 wt % ash, more preferably at most 5 wt % ash, most preferably at most 4.5 wt % ash; and
(d) preferably at most 8 wt % hemicelluloses (preferably xylans: polysaccharides predominantly having a backbone of β-D-xylose units with various side units such as arabinose, glucuronic acid and acetate; or mannans: polysaccharides having a backbone of mannose an glucose units, with possible galactose side units), more preferably at most 5 wt % xylan or mannan, even more preferably at most 4 wt % xylan or mannan, most preferably 1.0-3.0 wt % xylan or mannan.

Preferably, the composition is a cellulose pulp obtained from herbaceous biomass, including grasses and straws, more preferably from straw. Such pulp may also be referred to as "herbaceous biomass pulp" or "straw pulp" in the context of the invention. The cellulose pulp according to the invention is ideally suited to be used in enzymatic hydrolysis, as described further below.

Typically, the lignin liquor according to the invention comprises a higher degree of native lignin, when compared to prior art lignin liquors. Also the purity of the lignin containing liquor as well as the lignin precipitated from it is increased and the amount of impurity decreased. Without being bound to any theory, it is envisioned that fewer reactions take place between lignin and e.g. hemicellulose derivatives, degradation products thereof, or other reactive components present in the biomass such as proteins and other non-structural components, during the organosolv process according to the invention. These reactions are reduced in the process according to the invention by virtue of the prior extraction, which removes large parts of the non-structural components as extractives. This is especially true in case the process according to the invention is combined with low temperature organosolv, as at such reduced temperatures the hemicellulose or its monomeric derivatives (e.g. xylose, arabinose, mannose) is less prone to degrade, and thus less reactive towards lignin. In addition, removal of lipophilic extractives by virtue of the organic extraction prior to the organosolv step results in a reduced presence of such extractives in the liquor and reduced co-precipitation thereof during lignin precipitation.

Enzymatic Hydrolysis

In a preferred embodiment, the cellulose-enriched product stream (pulp), which is obtained as a product from the organosolv step, is subjected to enzymatic hydrolysis. Enzymatic hydrolysis of cellulose to glucose is accomplished by an enzyme or combination of enzymes, capable of hydrolysing cellulose, referred to as hydrolytic enzymes, preferably cellulases. Hydrolysis of cellulose is also known as cellulolysis. The activity of cellulase enzymes is typically measured in FPU (filter paper unit); see Ghose, T. K. Measurement of cellulase activities. *Pure Appl. Chem.* 1987, 59, 257-268.

The process according to the invention may be performed using any cellulase enzyme. Suitable cellulase enzymes are endocellulases (breaking cellulose at inner positions), exocellulases (cleaving cellulose at more external positions to produce cellobiose or cellutetraose), beta-glucosidases (cellobiases, cleaving the exocellulase products into glucose units). Other cellulase enzymes, such as oxidative cellulases and cellulose phosphorylases, are less preferred. Preferably a combination of cellulase enzymes is used, in particular a combination of endo-cellulase, exo-cellulase and β-glucosidase. Also, hemicellulases (e.g. xylanases, arabinases, mannanases, etc.) may be present to decompose any residual hemicellulose remaining after the organosolv step.

In the process according to the invention, the enzymatic hydrolysis of cellulose may be performed in any manner known in the art. Thus, the cellulose-enriched product stream or cellulose-rich pulp is brought in contact with an enzyme capable of hydrolysing cellulose, preferably a mixture of cellulases. The resulting hydrolysate is rich in glucose, which may be further processed, optionally after separation of solid residues, such as fermented to produce e.g. ethanol or other alcohols or thermally or chemically treated to produce e.g. 5-hydroxymethyl-furfural and other furans, or the glucose may be used as such, as known in the art.

The invention also relates to a process for the enzymatic hydrolysis of cellulose by bringing the cellulose pulp according to the invention, as described above, in contact with one ore more cellulase enzymes. Using the process according to the invention, a reduced load of hydrolytic enzymes is needed to achieve the same glucose yield, when compared to prior art processes for the enzymatic hydrolysis of cellulose, which reduces the costs of the enzymatic production of glucose from cellulose.

In case an aqueous pre-extraction step (i.e. the extracting liquid comprises below 20 wt % organic solvent) is part of the process according to the invention the aqueous extract, in particular a protein-containing aqueous extract, which is obtained by aqueous pre-extraction as described above, is beneficially used as supplement during enzymatic hydrolysis of the cellulose pulp. The presence of such an aqueous extract, optionally after (partial) concentration by methods known in the art, results in significant enhancement of the enzyme activity during enzymatic hydrolysis of cellulose. As such, the enzyme loading during enzymatic hydrolysis step can be significantly reduced, without negatively affecting the yield of glucose.

Surprisingly, the protein-rich aqueous biomass extract, suitable for enhancing the activity of the hydrolysing enzyme, may efficiently be prepared by extracting the biomass with water and subsequently filtering the mixture. No further purification steps are necessary for achieving a significant increase in enzyme activity during enzymatic hydrolysis. Other components, which may be co-extracted from the biomass during aqueous extraction, do not inhibit the hydrolytic enzyme (cellulase) during enzymatic hydrolysis of cellulose, or this inhibition is more than compensated by the activity raise caused by the presence of the aqueous extract. Protein from the biomass itself constitutes a relatively cheap and easily accessible protein source.

As a result of the (further) reduced enzyme requirement, this preferred embodiment of the present invention meets the need for reducing the costs of enzymatic hydrolysis of cellulose. Without being bound to a theory, the inventors assume that proteins from the aqueous extract are adsorbed to the lignin present in the cellulosic substrate. As such, the amount of hydrolytic enzyme inactivated by adsorption onto liberated lignin decreases. Thus, a cellulose-rich pulp, originating from pretreated biomass is contacted simultaneously with (i) an enzyme capable of hydrolysing cellulose, preferably a (mixture of) cellulase(s), and with (ii) a protein-rich aqueous extract originating from aqueous extraction of biomass. In an especially preferred embodiment, the biomass is pretreated according to the present invention, i.e. subjected to extraction and subsequent organosolv as described above, and the protein-rich aqueous biomass extract used during the enzymatic hydrolysis of biomass originates from aqueous extraction of the same biomass, prior to organosolv. The protein-rich extract may be the directly obtained extract or a concentrate thereof.

Further Process Steps

The cellulose-depleted product stream, resulting from separating off the cellulose-enriched stream subjected to enzymatic hydrolysis as described above, may be further treated or separated for the purpose of isolating other valuable products. In particular, the cellulose-depleted product stream (liquor), containing lignin, carbohydrates (notably hemicellulose and its degradation products), organic acids, salts and other compounds, may be depleted in lignin by precipitation of lignin through decreasing the organic solvent content of the liquor, e.g. by dilution with water and/or by evaporation of (non-hydroxylic and/or other) organic solvent, e.g. followed by centrifugation. The resulting liquid stream, which is depleted in cellulose and/or depleted in lignin, and which contains appreciable levels of hemicellulose derivatives, e.g. xylose and its oligomers and derivatives, such as furfural, may advantageously be subjected to process steps for recovering these compounds, such as isolating furfural and/or carbohydrates, chemical conversion of carbohydrates to furfural and subsequent separation of furfural, anaerobic treatment using an anaerobic culture from commercial anaerobic digestions or fermentations as a starting sludge.

The temperatures used in the anaerobic treatment are typical for mesophilic micro-organisms, i.e. between 15 and 55° C., preferably between 30 and 45° C. Biogas can be collected from the anaerobic treatment. Alternatively, anaerobic fermentation can be performed for converting the hemicellulose decomposition and possible other organic products to ethanol or other alcohols, by using yeasts capable of converting sugars to alcohols and carbon dioxide. The yeast may advantageously have been engineered to be capable of converting other specific sugars (e.g. xylose) from hemicelluloses to alcohols as well, e.g. by introducing xylose-isomerase and/or arabinose-converting enzymes into the yeast (see e.g. WO 03/062430, WO 2008/041840, WO 2010/074577).

EXAMPLES

The following examples are intended to illustrate the invention, not to limit the scope.

Example 1

(Pre-)Extraction+Low Temperature Organosolv+Enzymatic Hydrolysis

A first batch (batch 1) of wheat straw was pre-extracted using 10 L water per kg biomass. A second batch (batch 2) of wheat straw was first pre-extracted using the same conditions as for the first batch, and subsequently extracted with 10 L ethanol (containing about 4 wt % water) per kg biomass. Both pre-extraction and extraction were performed using a Soxhlet extractor. Both batches 1 and 2 of wheat straw were subjected to organosolv, as well as a batch of wheat straw, which has not undergone (pre-)extraction (control). Organosolv conditions employed: 140° C.; 120 min; solvent=ethanol/water (60/40 w/w); liquid/solid ratio=10 L/kg; 50 mM $H_2SO_4$ for the (pre-)extracted wheat straw; 60 mM $H_2SO_4$ for the control experiment. The increased $H_2SO_4$ concentration for the control experiment is to counteract the higher acid-neutralisation capacity of the mineral part of the original biomass, which is lowered during pre-extraction by (partial) removal of the mineral part.

During organosolv of the control experiment, formation of balls of fatty acids and/or waxy material was observed, which hindered the fractionation of straw into the lignin-enriched liquor and the cellulose-enriched pulp, giving i.a. rise to a lower cellulose content of the pulp. These balls were not observed during organosolv of the second batch of extracted wheat straw.

The negative effects of the extractives present in biomass on organosolv are reflected in the pulp yield, xylan hydrolysis and delignification degrees obtained in the organosolv process, as shown in table 2, and in the compositions of the cellulose pulp obtained during organosolv, as shown in table 3. Compositions are determined using the method described in W. J. J. Huijgen, A. T. Smit, P. J. de Wild, H. den Uil, *BioResource Technology*, 2012, 114, 389-398. The four components of the pulp given in Table 3 make up approximately 90 wt % of the pulp, and the remaining 10 wt % may include uronic acids, acetyl groups and extractives (non-structural components such as peptides, lipids, DNA, chlorophyll).

TABLE 2

Pulp yield and fractionation degrees

|  | control | batch 1 | batch 2 |
| --- | --- | --- | --- |
| Biomass recovery after extraction | N.A. | 91.7 wt % | 87.6 wt % |
| Pulp yield* | 50.4 wt % | 47.6 wt % | 40.2 wt % |
| Xylan hydrolysis** | 78.5% | 82.4% | 92.8% |
| Delignification*** | 73.9% | 70.8% | 87.5% |

*Based on dry weight of the fresh biomass before (pre-)extraction.
**Degree of xylan hydrolysis, based on amount of xylan present in the fresh biomass.
***Degree of lignin removal, based on lignin present in the fresh biomass.

TABLE 3

Cellulose pulp composition (in wt % based on dry weight)

| component | control | batch 1 | batch 2 |
| --- | --- | --- | --- |
| glucan | 63.8 | 68.7 | 78.9 |
| xylan | 8.5 | 7.4 | 3.5 |
| lignin | 9.2 | 10.8 | 5.5 |
| ash | 6.8 | 4.5 | 4.6 |

Pulp yields are higher for the control experiment and the water pre-extracted batch 1, which are indicative of a less effective fractionation (i.e. more impurities are present in the cellulose pulp). This is confirmed in the degree of delignification and xylan hydrolysis, and in the compositions of the pulp, as shown in table 3. Ethanol extraction prior to organosolv results in a cellulose pulp comprising significantly increased amount of cellulose and significantly decreased amounts of lignin and xylan, when compared with cellulose pulp obtained by organosolv of biomass pre-extracted with water or not (pre-)extracted at all. Water pre-extraction leads to a significant reduction in ash content of the cellulose pulp. In addition, water pre-extraction and ethanol extraction give rise to more hydrolysis of the hemicellulose (xylan) during organosolv. Reduced amounts of lignin imply a more effective fractionation or delignification of the biomass (separation of lignin from cellulose).

Figure 1:
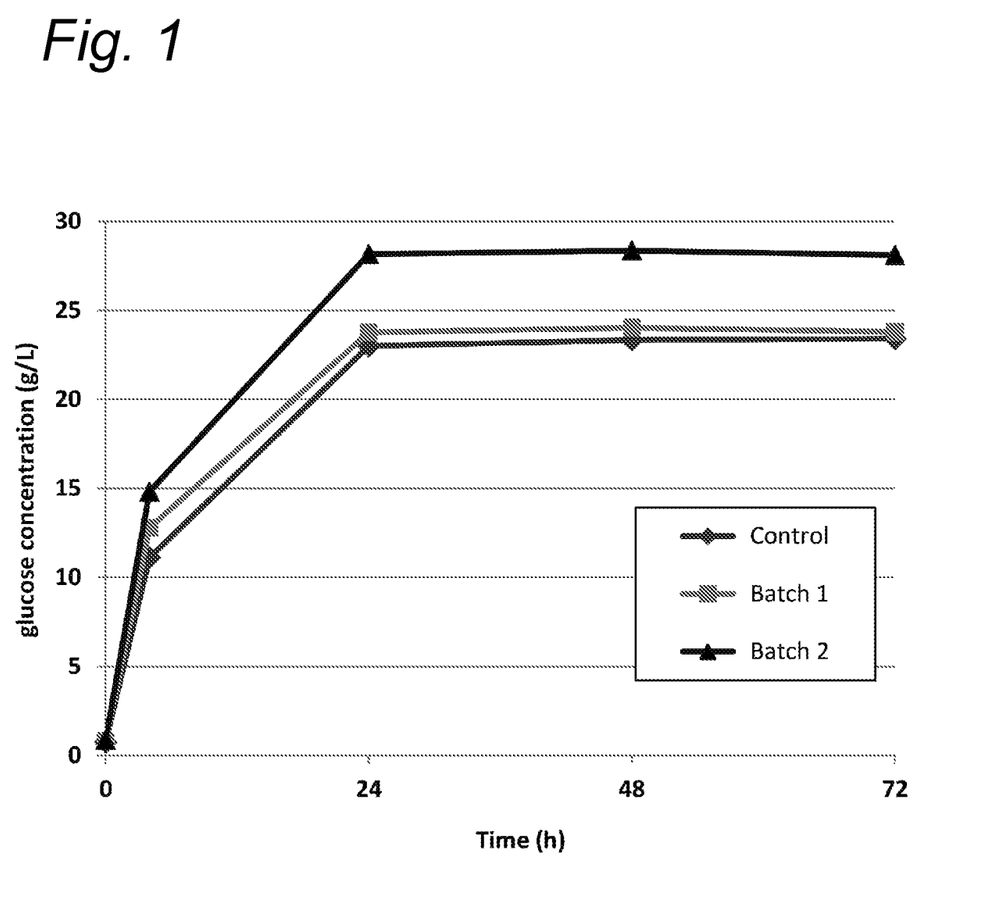
FIG. 1 summarizes the results obtained from the enzymatic hydrolysis of example 1 (batch 1=aqueous extracted biomass, batch 2=aqueous and organic extracted biomass, control=non-extracted biomass).

The cellulose-enriched pulp was subsequently subjected to enzymatic hydrolysis (conditions: 20 FPU per gram pulp of cellulase enzyme (ACCELLERASE® 1500, cellulase enzyme composition from DuPont Industrial Biosciences); 1.50 g pulp per 50.0 mL water buffered at pH 4.8; time=72 h). The progress of the enzymatic hydrolysis was monitored by determination of the glucose concentration at various intervals for 72 h. FIG. 1 summarizes the results obtained using the cellulose-enriched pulp, obtained by organosolv of batch 1, batch 2 and the control experiment. Water pre-extraction (batch 1) slightly increases the final glucose concentration, when compared to the control experiment, while ethanol extraction (batch 2) markedly increases the obtained final glucose concentration. Thus, employing organic extraction prior to organosolv increases the glucose concentration during enzymatic hydrolysis. Notably, in all experiments the final glucose concentration was already achieved after 24 h, which implies that the cellulose in the pulp obtained by the low temperature organosolv process of this example is readily accessible by the cellulase enzyme. Thus, the organosolv process is efficiently performed at reduced temperatures, such as at 140° C. or lower, preferably in combination with organic extraction prior to organosolv.

Example 2

(Pre-)Extraction+Organosolv

Two batches (batches 1 and 3) of wheat straw (<1 cm) were pre-extracted using 10 L water per kg biomass and subsequently extracted with 10 L ethanol (containing about 4 wt % water) per kg biomass. Two other batches (batches 2 and 4) of wheat straw were not extracted (control). Both pre-extraction and extraction of batches 1 and 3 were performed in a counter-current stage-wise mode. All batches 1-4 of wheat straw were subjected to organosolv. Organosolv conditions employed for batches 1 and 2: low temperature organosolv at 140° C.; 90 min; solvent=ethanol/water (60/40 w/w); liquid/solid ratio=5 L/kg; 100 mM $H_2SO_4$ for the (pre-)extracted batch 1; 120 mM $H_2SO_4$ for the control batch 2. Organosolv conditions employed for batches 3 and 4: high temperature organosolv at 190° C.; 60 min; solvent=ethanol/water (60/40 w/w); liquid/solid ratio=5 L/kg; 30 mM $H_2SO_4$ for the (pre-)extracted batch 3; 60 mM $H_2SO_4$ for the control batch 2. The increased $H_2SO_4$ concentration for the control experiment is to counteract the higher acid-neutralisation capacity of the mineral part of the original biomass, which is lowered during pre-extraction by (partial) removal of the mineral part. In order to ensure proper wetting of the biomass when using a liquid-solid ratio of 5 L/kg, the wheat straw was placed in a porous metal basket and compressed with a mechanical press. The basket was placed in the autoclave below the level of the liquor. The liquid-solid ratio of 5 L/kg refers to the overall ratio in the autoclave.

The negative effects of the extractives present in biomass on organosolv are reflected in the pulp yield and delignification degrees obtained in the organosolv process, as shown in table 4, and in the compositions of the cellulose pulp obtained during organosolv, as shown in table 5. Compositions are determined using the method described in W. J. J. Huijgen, A. T. Smit, P. J. de Wild, H. den Uil, *BioResource Technology*, 2012, 114, 389-398. The four components of the pulp given in Table 5 make up approximately 90 wt % of the pulp, and the remaining 10 wt % may include uronic acids, acetyl groups and extractives (non-structural components such as peptides, lipids, DNA, chlorophyll).

TABLE 4

Pulp yield and fractionation degrees

| | batch 1 | batch 2 | batch 3 | batch 4 |
| --- | --- | --- | --- | --- |
| Biomass recovery after extraction | 90.6 wt % | N.A. | 90.6 wt % | N.A. |
| Pulp yield* | 41.7 wt % | 48.7 wt % | 39.0 wt % | 46.4 wt % |
| Delignification** | 83.6% | 76.0% | 78.4% | 72.6% |
| Xylan hydrolysis*** | 86.7% | 72.3% | 95.9% | 79.5% |
| lignin yields**** | | | | |
| in pulp | 16.4 wt % | 24.0 wt % | 21.6 wt % | 27.4 wt % |
| from liquor | 71.2 wt % | 84.0 wt % | 72.4 wt % | 90.2 wt % |

*Based on dry weight of the fresh biomass before (pre-)extraction.
**Degree of lignin removal, based on lignin present in the fresh biomass.
***Degree of xylan hydrolysis based on amount of xylan present in the fresh biomass.
****Lignin mass balance, based on total weight of lignin present in the fresh biomass.
Some residual lignin was found in the pulp (see also table 5). The remainder ended up in the liquor and was precipitated by addition of the liquor to 3 parts of water per part of liquor (w/w).

TABLE 5

Cellulose pulp composition (in wt % based on dry weight)

| Component | batch 1 | batch 2 | batch 3 | batch 4 |
| --- | --- | --- | --- | --- |
| Glucan | 71.2 | 65.0 | 76.5 | 64.8 |
| Xylan | 7.3 | 13.0 | 2.4 | 10.1 |
| Lignin | 6.3 | 7.9 | 8.9 | 9.4 |
| Ash | 4.6 | 6.3 | 4.3 | 7.5 |

Both for low temperature as for high temperature organosolv, pulp yields are higher for the control experiments, which is indicative of a less effective fractionation (i.e. more impurities are present in the cellulose pulp). This is confirmed in the degree of delignification and xylan hydrolysis, which are higher for the (pre-)extracted batches, and in the compositions of the pulp, as shown in table 5. Extraction prior to organosolv results in a cellulose pulp comprising significantly increased amount of cellulose (based on measured glucose monomeric units) and significantly decreased amounts of lignin, xylan and ash, when compared with cellulose pulp obtained by organosolv of non-extracted wheat straw. Reduced amounts of lignin imply a more effective fractionation or delignification of the biomass (separation of lignin from cellulose). It is expected that the pulp obtained from batch 1 and 3 performs better in the enzymatic hydrolysis, compared to the pulp obtained form batch 2 and 4 respectively, in line with the results of example 1. The lignin mass balances in table 4 confirm that much less lignin ended up in the pulp when extraction was performed prior to organosolv. Notably, the total weight of the lignin obtained after organosolv exceeded 100 wt % for the control experiments, which indicates that the formation of "pseudolignin" (due to many reactions occurred during organosolv between lignin and for example non-structural components from the biomass and degradation products of e.g. xylan), and/or significant co-precipitation of lipophilic extractives such as waxes and fatty acids.

Although the pulp obtained from extracted biomass using high temperature organosolv at 190° C. contained the highest amount of glucan, lower amounts of lignin were surprisingly found for the low temperature organosolv pulp, matching the highest degree of delignification for batch 1 in table 4. Thus, although it is generally established in the art that the effectiveness of the organosolv fractionation decreases with decreasing temperature, it is now surprisingly found that organosolv can also be performed at lower temperatures such as 140° C. with excellent fractionation, especially when an extraction step is performed prior to the organosolv step. The results of example 2 also demonstrate that the process according to the invention provides excellent fractionation even when the more challenging condition of using 5 L treatment liquid per kg biomass (liquid/solid ratio=5 L/kg) is applied. It is generally accepted that the extent of fractionation decreases but the industrial applicability increases when the amount of treatment liquid per kg biomass decreases. The process according to the invention thus provides effective organosolv fractionation even at the reduced temperature of 140° C. and at a liquid/solid ratio of 5 L treatment liquid per kg biomass.

Example 3

(Pre-)Extraction+Low Temperature Organosolv+Enzymatic Hydrolysis

Wheat straw was chopped into pieces of about 1 cm length, and was divided into eight batches which received different treatments as summarised in Table 6. Pre-extraction was performed on batches 2, 5 and 7, which involved extraction with 10 L water per kg biomass, and subsequently with 10 L ethanol or acetone per kg of the original biomass prior to aqueous extraction. Both pre-extraction and extraction of batches 1 and 3 were performed in a counter-current stage-wise mode. Batches 1-8 were subsequently subjected to organosolv at the indicated temperature, using the solvent system and treatment time as given in Table 6. The liquid/solid ratio was 10 L per kg biomass. Sulfuric acid was added to the treatment liquid of batches 1-7. The increased $H_2SO_4$ concentration for the batches which did not undergo pre-extraction (1, 3, 4, 6) was applied to counteract the higher acid-neutralisation capacity of the mineral part of the original biomass, which is otherwise lowered during pre-extraction by (partial) removal of the mineral part. For batch 8, no acid was added, and organosolv was performed auto-catalytically at a temperature of 205° C. Batch 1 is identical to the control of example 1, and batch 2 is identical to batch 2 of example 1.

TABLE 6

Pre-extraction and treatment conditions of wheat straw

| | | | organosolv | | |
|---|---|---|---|---|---|
| batch | pre-extraction | t (min) | T (° C.) | solvent system (w/w) | $H_2SO_4$ (mM) |
| 1 | no | 120 | 140 | ethanol/water (60/40) | 60 |
| 2 | water; ethanol | 120 | 140 | ethanol/water (60/40) | 50 |
| 3 | no | 120 | 140 | acetone/water (50/50) | 60 |
| 4 | no | 60 | 140 | acetone/water (50/50) | 60 |
| 5 | water; acetone | 60 | 140 | acetone/water (50/50) | 50 |
| 6 | no | 60 | 140 | acetone/water (60/40) | 60 |
| 7 | water; acetone | 60 | 140 | acetone/water (60/40) | 50 |
| 8 | no | 60 | 205 | acetone/water (50/50) | 0 |

During organosolv with ethanol/water as treatment liquid (batch 1), the formation of balls of fatty acids and/or waxy material was observed, which hindered the fractionation of straw into the lignin-enriched liquor and the cellulose-enriched pulp, giving i.a. rise to a lower glucan concentration in the pulp. Only when pre-extracted biomass was subjected to ethanol/water organosolv (batch 2), no waxy balls were observed. In batches 3-7, wherein acetone/water was used as treatment liquid, no such balls were observed, even without pre-extraction.

The results of the organosolv regarding the pulp are given in Table 7. Pulp yields, delignification percentages and pulp compositions are acceptable for all experiments. Surprisingly, the additional step of pre-extracting the biomass gave a greater extent of delignification and higher glucan purity of the pulp compared to non-pre-extracted biomass. This applies both to the ethanol organosolv (batch 2 vs. batch 1) and to the acetone organosolv (batch 5 vs. batch 4 and batch 7 vs. batch 6). Reducing the reaction time from 120 to 60 minutes of acetone organosolv (batches 3 vs. 4) gave surprisingly similar results in terms of delignification and pulp compositions, while pulp yield increases. High temperature organosolv (batch 8) gave similar results in terms of pulp composition and delignification, indicating that reducing the temperature does not negatively affect the performance of the organosolv fractionation.

The form of the lignin (hydroxyl content) obtained as precipitate from the liquor obtained after organosolv is also given in Table 7. First of all, the lignin obtained by low temperature organosolv with acetone shows an increased content of hydroxyl groups, when compared to low temperature organosolv with ethanol as solvent, indicative of more native lignin and reduced formation of pseudo-lignins. In addition, the hydroxyl content of the lignin is markedly increased when compared to lignin obtained with high temperature organosolv at about 200° C., which is about 4 mmol/g lignin. The hydroxyl content of the lignin was determined via the wet chemical method as described by Zakis et al., "Functional analysis of lignins and their derivatives", TAPPI Press, Atlanta, 1994, page 94.

Compositions were determined using the method described in W. J. J. Huijgen, A. T. Smit, P. J. de Wild, H. den Uil, BioResource Technology, 2012, 114, 389-398. The four components of the pulp given in Table 7 make up approximately 90 wt % of the pulp, and the remaining 10 wt % may include uronic acids, acetyl groups and extractives (non-structural components such as peptides, lipids, DNA, chlorophyll).

TABLE 7

Pulp yield and composition, hydroxyl content of lignin

| | pulp yield | delignification | | pulp composition (wt %)**** | | | |
|---|---|---|---|---|---|---|---|
| batch | (wt %)* | (%)** | OH*** | glucan | xylan | lignin | ash |
| 1 | 50.4 | 73.9 | 6.0 | 63.8 | 8.5 | 9.2 | 6.8 |
| 2 | 40.2 | 87.5 | 6.4 | 78.9 | 3.5 | 5.5 | 4.6 |
| 3 | 43.0 | 73.1 | 6.9 | 73.9 | 3.1 | 11.0 | 3.2 |
| 4 | 50.1 | 69.8 | 6.7 | 68.6 | 6.5 | 10.6 | 5.3 |
| 5 | 43.0 | 82.1 | 7.9 | 75.8 | 3.9 | 7.3 | 6.0 |
| 6 | 48.6 | 74.2 | 5.7 | 69.1 | 5.6 | 9.4 | 6.5 |
| 7 | 42.0 | 84.3 | 7.0 | 77.8 | 3.2 | 6.6 | 4.9 |
| 8 | 48.7 | 78.6 | nd | 65.4 | 7.8 | 7.0 | 11.1 |

*Based on dry weight of the fresh biomass, before pre-extraction.
**Degree of lignin removal, based on lignin present in the fresh biomass.
***OH content in mmol per g lignin; nd = not determined.
****Based on dry weight of cellulose pulp.

Some xylan and glucan degradation products were detected in the lignin-containing liquor. The products obtained from xylan and glucan are given in Table 8, in xylose and glucose equivalents respectively. In general, more residual xylan is found in the pulp when no pre-extraction is performed, when ethanol is used instead of acetone (batches 1 and 2), and when organosolv is performed autocatalytically at high temperature (batch 8). The hydrolysis and degradation products of xylan are found in the liquor. Importantly, the yield of monomeric xylose is greatly increased when ethanol is replaced by acetone, and no ethyl xylosides are formed using low temperature organosolv with acetone. Some furfural is detected in all liquors. Most, if not all of the remaining hemicellulose will have been converted to soluble xylooligosaccharides (XOS), which end up in the liquor. Regarding the glucan products, the major difference between ethanol and acetone as organic solvent is the formation of glucosides in the hydroxylic solvent, while no ethylglucosides are formed using the non-hydroxylic solvent.

The most significant effect associated with reducing the temperature of the organosolv reaction from 205° C. to 140° C. is the increase in xylose yield, while the xylan hydrolysis degree remains more or less the same. This indicates that xylan degrades beyond its monomeric sugars at high temperature into undesirable by-products which have not been measured. Likewise, glucan is degraded to some extent at high temperature, and the degradation products are not retrieved as glucose monomers or hydroxymethylfuran (HMF). Thus, the glucose monomers that are formed during organosolv degrade into undesirable by-products at 205° C.

TABLE 8

Distribution of xylan and glucan products

| | xylan (%)* | | | | glucan (%)** | | | |
|---|---|---|---|---|---|---|---|---|
| batch | xylan | Xyl | furfural | EX | glucan | Glc | HMF | EG |
| 1 | 21.5 | 32.9 | 7.7 | 38.1 | 90.7 | 2.5 | bdl | 4.6 |
| 2 | 7.2 | 36.9 | 11.1 | 46.6 | 89.5 | 3.0 | bdl | 5.4 |
| 3 | 6.8 | 81.3 | 15.4 | — | 89.8 | 7.3 | 0.8 | — |
| 4 | 16.4 | 73.2 | 7.3 | — | 97.2 | 5.6 | 0.5 | — |
| 5 | 8.4 | 76.7 | 9.7 | — | 92.1 | 5.6 | 0.3 | — |
| 6 | 13.6 | 71.9 | 9.4 | — | 94.8 | 5.7 | 0.5 | — |
| 7 | 6.7 | 70.2 | 12.6 | — | 92.4 | 6.0 | 0.5 | — |
| 8 | 17.7 | 0.6 | 3.8 | — | 92.0 | bdl | 0.2 | — |

*In xylose equivalents; moles of product based on total moles of xylose monomeric units present in xylan in the fresh biomass, before pre-extraction. Total percentages above 100% result from measuring inaccuracies. Xylan is found in the pulp, the rest in the liquor. Xyl = xylose; EX = ethyl xylosides;
**In glucose equivalents; moles of product based on total moles of glucose monomeric units present in glucan in the fresh biomass, before pre-extraction. Total percentages above 100% result from measuring inaccuracies. Glucan is found in the pulp, the rest in the liquor. Glc = glucose; HMF = 5-hydroxymethyl-furfural; EG = ethyl-glucosides; bdl = below detection limit.

Figure 2:
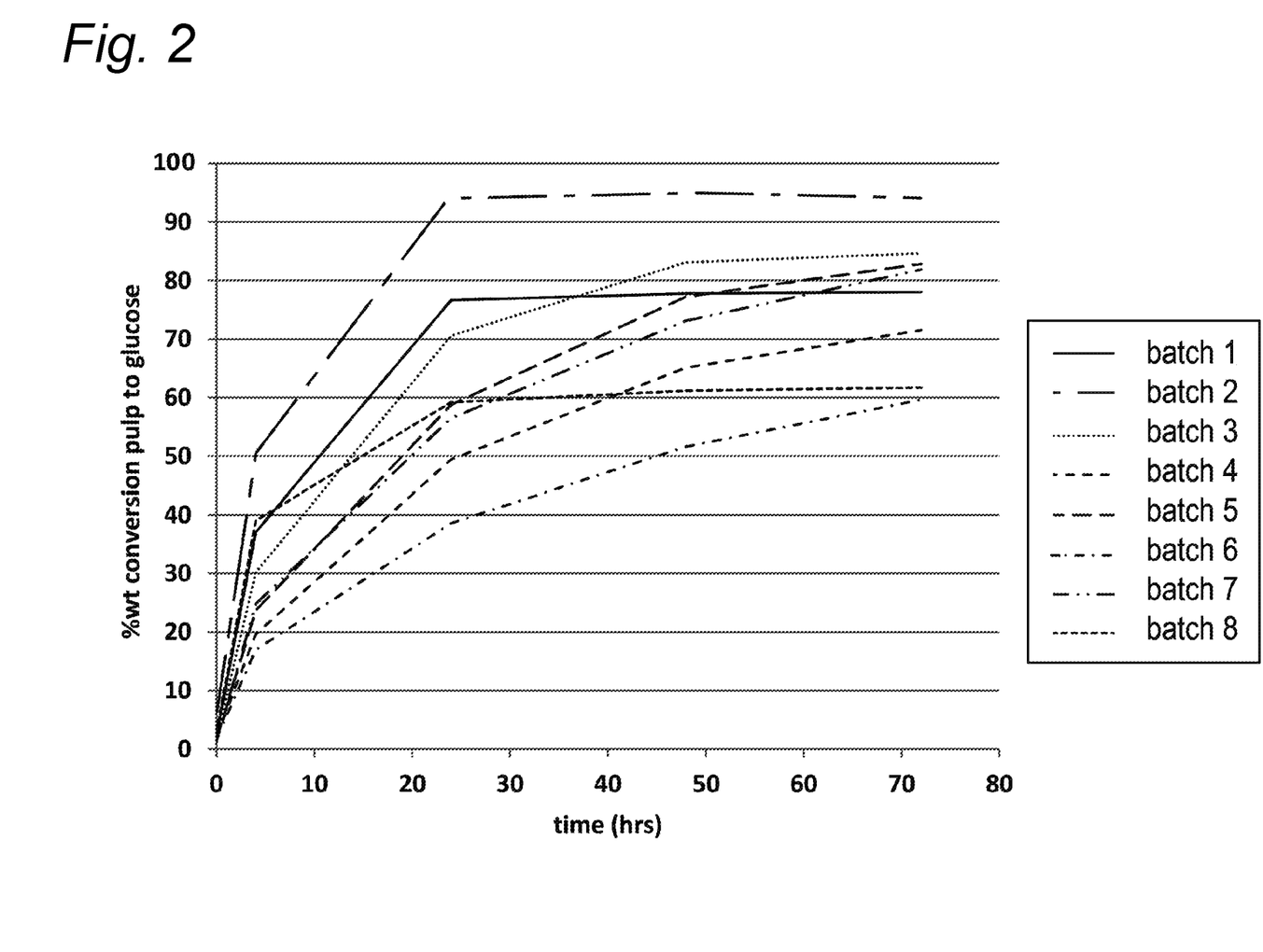
FIG. 2 summarizes the results obtained from the enzymatic hydrolysis of example 3.

The cellulose-enriched pulp obtained by organosolv fractionation of each of the batches was subsequently subjected to enzymatic hydrolysis. Conditions: 10 FPU per gram pulp (for batches 1 and 2: 20 FPU/g, for batch 8: 38 FPU/g) of cellulase enzyme (ACCELLERASE® 1500 (batches 1-7) or ACCELLERASE® 1000 (batch 8), cellulase enzyme composition from DuPont Industrial Biosciences); 1.50 g pulp (dry weight) per 50.0 mL water buffered at pH 4.8; time=72 h. The progress of the enzymatic hydrolysis was monitored by determination of the glucose yield (as wt % based on total dry weight of the pulp at t=0 h) at various intervals up to t=72 h. FIG. 2 summarises the results obtained using the cellulose-enriched pulp obtained by organosolv of batches 1-8. Maximum glucose conversion values for batches 1, 2 and 8 were obtained after 24 h, in view of the increased enzyme load. The cellulose pulp obtained by organosolv at reduced temperatures is readily hydrolysed with a relatively low enzyme load of 10 FPU/g. Batches 4-7, subjected to low temperature organosolv with acetone for 60 minutes, were hydrolysed more or less similarly to batch 3 which was subjected to organosolv for 120 minutes. From a cost-effectiveness point of view, it is beneficial to perform the organosolv reaction for a shorter period of time, for which the process according to the invention is well suited.

The pulp obtained with high temperature organosolv gave a lower yield in glucose, especially since the final conversion was already obtained after 24 h, while the other batches did not reach the final glucose conversion at the end of the measurement at t=72 h. The pulp obtained by ethanol organosolv of non-pre-extracted biomass (batch 1) gave slightly lower glucose yield than the pulp obtained by acetone organosolv of batches 3, 5 and 7, especially in view of the expected further conversion of these batches after t=72 h. The pulp obtained from ethanol organosolv of pre-extracted biomass (batch 2) gave the highest glucose yield, based on total weight of the pulp, which is due to its high glucan content (see Table 7) and a higher enzyme activity. The total glucose yield based on the glucan present in the fresh biomass is more or less similar for all experiments. Thus, it is concluded that the organosolv process is efficiently performed at reduced temperatures, such as at 140° C. or lower, using acetone as organic solvent, and that the cellulose pulps obtained therewith are efficiently hydrolysed to glucose.

The invention claimed is:

1. A process for fractionating lignocellulosic biomass, comprising:
    (a) extracting the biomass, in fresh or dried form, with an extracting liquid comprising at least 50 wt % of a first organic solvent selected from lower alcohols and ketones at a temperature between 15° C. and 80° C., wherein the amount of extracting liquid is 0.5-20 L per kg biomass;
    (b) separating the extraction liquid from the extracted biomass, wherein the extraction liquid comprises lipophilic extractives selected from lipophilic proteins, fatty acids, triglycerides, waxes, terpenes, and resin acids; and
    (c) subjecting the extracted biomass from (b) to organosolv with a treatment liquid comprising a second organic solvent selected from lower alcohols, ethers and ketones, water and optionally an acid, at a temperature between 120° C. and 280° C., wherein a pulp comprising less lignin than the biomass and a liquor comprising lignin are obtained.

2. The process according to claim 1, wherein the first organic solvent comprises ethanol or acetone.

3. The process according to claim 2, wherein the first organic solvent comprises ethanol.

4. The process according to claim 1, wherein the extracting liquid comprises between 0 and 30 vol. % of water.

5. The process according to claim 1, wherein the extraction (a) is performed at a temperature between 30° C. and 75° C.

6. The process according to claim 1, wherein the treatment (c) is performed at a temperature between 125° C. and 250° C.

7. The process according to claim 1, wherein the treatment (c) is performed at a temperature between 120° C. and 170° C.

8. The process according to claim 1, wherein the first organic solvent is the same as the second organic solvent.

9. The process according to claim 8, wherein both the first and the second solvent comprise ethanol or acetone.

10. The process according to claim 1, wherein the extraction (a) is preceded by a pre-extraction in which the biomass is extracted with water at a temperature between 20° C. and 100° C., to obtain an extract comprising hydrophilic extractives selected from salts and water-soluble proteins.

11. The process according to claim 10, wherein the pre-extraction temperature is between 20° C. and 60° C.

12. The process according to claim 1, wherein the lignocellulosic biomass is selected from herbaceous biomass, softwood, hardwood and combinations thereof.

13. The process according to claim 12, wherein the second organic solvent is selected from lower alcohols and ethers.

14. The process according to claim 1, wherein the treatment liquid comprises:
    (i) 25-80 wt % of the second organic solvent, based on total weight of the treatment liquid;
    (ii) 20-75 wt % water, based on total weight of the treatment liquid; and
    (iii) at most 500 g of an acid, per kg dry weight of the biomass.

15. The process according to claim 1, further comprising:
    (d) subjecting the pulp to enzymatic hydrolysis.

16. A process for fractionation of herbaceous biomass, comprising:
    (a) extracting the biomass, in fresh or dried form, with an extracting liquid comprising at least 50 wt % of a first organic solvent selected from lower alcohols and ketones at a temperature between 15° C. and 80° C., wherein the amount of extracting liquid is 0.5-20 L per kg biomass;

(b) separating the extraction liquid from the extracted biomass, wherein the extraction liquid comprises lipophilic extractives selected from lipophilic proteins, fatty acids, triglycerides, waxes, terpenes, and resin acids; and (c) subjecting the extracted biomass from (b) to organosolv with a treatment liquid comprising a second organic solvent selected from lower alcohols, ethers and ketones, and further comprises water and an acid, at a temperature between 120° C. and 170° C., and at a pH between 1 and 5, wherein a pulp comprising less lignin than the biomass and a liquor comprising lignin are obtained.

17. The process according to claim 16, further comprising:

(d) subjecting the pulp to enzymatic hydrolysis.

18. The process according to claim 16, wherein the extraction (a) is preceded by a pre-extraction in which the biomass is extracted with water at a temperature between 20° C. and 100° C., and the hydrolysis (d) is performed in the presence of an aqueous extract obtained in pre-extraction.

19. The process according to claim 12, wherein the lignocellulosic biomass comprises herbaceous biomass.

20. The process according to claim 1, wherein the fresh or dried biomass is chopped or milled prior to (a).

21. The process according to claim 16, wherein the fresh or dried biomass is chopped or milled prior to (a).

22. The process according to claim 16, wherein the extraction (a) is performed at a temperature between 30° C. and 60° C.

23. The process according to claim 5, wherein the extraction (a) is performed at a temperature between 30° C. and 60° C.

* * * * *